United States Patent
Ohishi

(10) Patent No.: US 11,490,871 B2
(45) Date of Patent: Nov. 8, 2022

(54) BLOOD FLOW FUNCTION EXAMINATION APPARATUS AND X-RAY DIAGNOSTIC APPARATUS

(71) Applicant: Toshiba Medical Systems Corporation, Otawara (JP)

(72) Inventor: Satoru Ohishi, Otawara (JP)

(73) Assignee: Canon Medical Systems Corporation, Otawara (JP)

(*) Notice: Subject to any disclaimer, the term of this patent is extended or adjusted under 35 U.S.C. 154(b) by 666 days.

(21) Appl. No.: 14/725,504

(22) Filed: May 29, 2015

(65) Prior Publication Data

US 2015/0257725 A1 Sep. 17, 2015

Related U.S. Application Data

(63) Continuation of application No. PCT/JP2013/082271, filed on Nov. 29, 2013.

(30) Foreign Application Priority Data

Nov. 29, 2012 (JP) .............................. JP2012-261261
Nov. 29, 2013 (JP) .............................. JP2013-248264

(51) Int. Cl.
  *A61B 6/00* (2006.01)
  *A61B 6/12* (2006.01)
  (Continued)

(52) U.S. Cl.
  CPC .............. *A61B 6/541* (2013.01); *A61B 5/026* (2013.01); *A61B 5/0215* (2013.01);
  (Continued)

(58) Field of Classification Search
  None
  See application file for complete search history.

(56) References Cited

U.S. PATENT DOCUMENTS 6,354,999 B1 * 3/2002 Dgany .................. A61B 1/015
                                                        600/486
7,343,195 B2 * 3/2008 Strommer ............ A61B 8/4227
                                                        600/453
(Continued)

FOREIGN PATENT DOCUMENTS

JP      08-332191 A    12/1996
JP      11-033004 A    2/1999
(Continued)

OTHER PUBLICATIONS

Machine Translation of JP 08-332191. Retrieved May 25, 2018 from https://dossier1.j-platpat.inpit.go.jp/tri/all/odse/ODSE_GM101_Top.action.*

(Continued)

*Primary Examiner* — Luther Behringer
(74) *Attorney, Agent, or Firm* — Oblon, McClelland, Maier & Neustadt, L.L.P.

(57) ABSTRACT

According to one embodiment, there is provided an X-ray diagnostic apparatus which comprises an X-ray generation unit configured to irradiate an object with X-rays; an X-ray detection unit configured to detect X-rays applied by the X-ray generation unit and transmitted through the object; an image generation unit configured to generate an X-ray image based on X-rays detected by the X-ray detection unit; a recording unit configured to record pressure data acquired by using a pressure sensor provided on a guide wire; a measurement position setting unit configured to set a measurement position for a pressure by the pressure sensor using the X-ray image; and a display unit configured to display the X-ray image almost in real time and superimpose and display the measurement position set by the measurement position setting unit.

17 Claims, 5 Drawing Sheets

(51) Int. Cl.
  *A61B 5/0215* (2006.01)
  *A61B 5/00* (2006.01)
  *A61B 5/026* (2006.01)
  *A61B 5/055* (2006.01)
  *A61B 6/03* (2006.01)
  *A61B 5/318* (2021.01)
(52) U.S. Cl.
  CPC .............. *A61B 5/6851* (2013.01); *A61B 6/12* (2013.01); *A61B 6/4417* (2013.01); *A61B 6/463* (2013.01); *A61B 6/503* (2013.01); *A61B 6/504* (2013.01); *A61B 5/055* (2013.01); *A61B 5/318* (2021.01); *A61B 6/032* (2013.01); *A61B 6/4225* (2013.01); *A61B 6/4233* (2013.01); *A61B 6/4441* (2013.01); *A61B 6/481* (2013.01); *A61B 6/486* (2013.01); *A61B 2560/0223* (2013.01)

(56) References Cited

U.S. PATENT DOCUMENTS

| | | | | |
|---|---|---|---|---|
| 8,804,901 | B2* | 8/2014 | Maurer, Jr. ............ | A61B 6/025 378/25 |
| 9,339,348 | B2* | 5/2016 | Davies .................. | A61B 34/10 |
| 2002/0049375 | A1* | 4/2002 | Strommer ............ | A61B 8/0833 600/407 |
| 2006/0100515 | A1* | 5/2006 | Nakata ..................... | A61B 8/06 600/441 |
| 2006/0241465 | A1 | 10/2006 | Huennekens et al. | |
| 2007/0129626 | A1 | 6/2007 | Mahesh et al. | |
| 2007/0201609 | A1 | 8/2007 | Ohishi et al. | |
| 2008/0247506 | A1* | 10/2008 | Maschke ................. | A61B 6/12 378/15 |
| 2010/0234698 | A1 | 9/2010 | Manstrom et al. | |
| 2011/0306867 | A1* | 12/2011 | Gopinathan .......... | A61B 5/064 600/407 |
| 2011/0319752 | A1 | 12/2011 | Steinberg et al. | |
| 2012/0008735 | A1* | 1/2012 | Maurer .................. | A61B 6/025 378/5 |
| 2013/0046190 | A1* | 2/2013 | Davies ............... | A61B 5/02007 600/486 |
| 2013/0116737 | A1* | 5/2013 | Edwards .............. | A61B 5/4041 607/2 |

FOREIGN PATENT DOCUMENTS

| | | |
|---|---|---|
| JP | 11-076183 A | 3/1999 |
| JP | 11-244248 A | 9/1999 |
| JP | 2003-265617 A | 9/2003 |
| JP | 2007-144180 A | 6/2007 |
| JP | 2007-229473 A | 9/2007 |
| JP | 2008-526387 A | 7/2008 |
| JP | 2011-36417 A | 2/2011 |
| JP | 2012-501807 A | 1/2012 |

OTHER PUBLICATIONS

Berne & Levy Physiology, 6th edition. 2008. pp. 322-324. (Year: 2008).*
International Search Report dated Mar. 4, 2014 in PCT/JP2013/082271 filed Nov. 29, 2013.
Japanese Office Action dated Jul. 11, 2017 in Japanese Patent Application No. 2013-248264.
Japanese Office Action dated Mar. 6, 2018 in Japanese Patent Application No. 2013-248264, 7 pages.
International Written Opinion dated Mar. 4, 2014 in PCT/JP2013/082271 filed Nov. 29, 2013 with English translation.

* cited by examiner

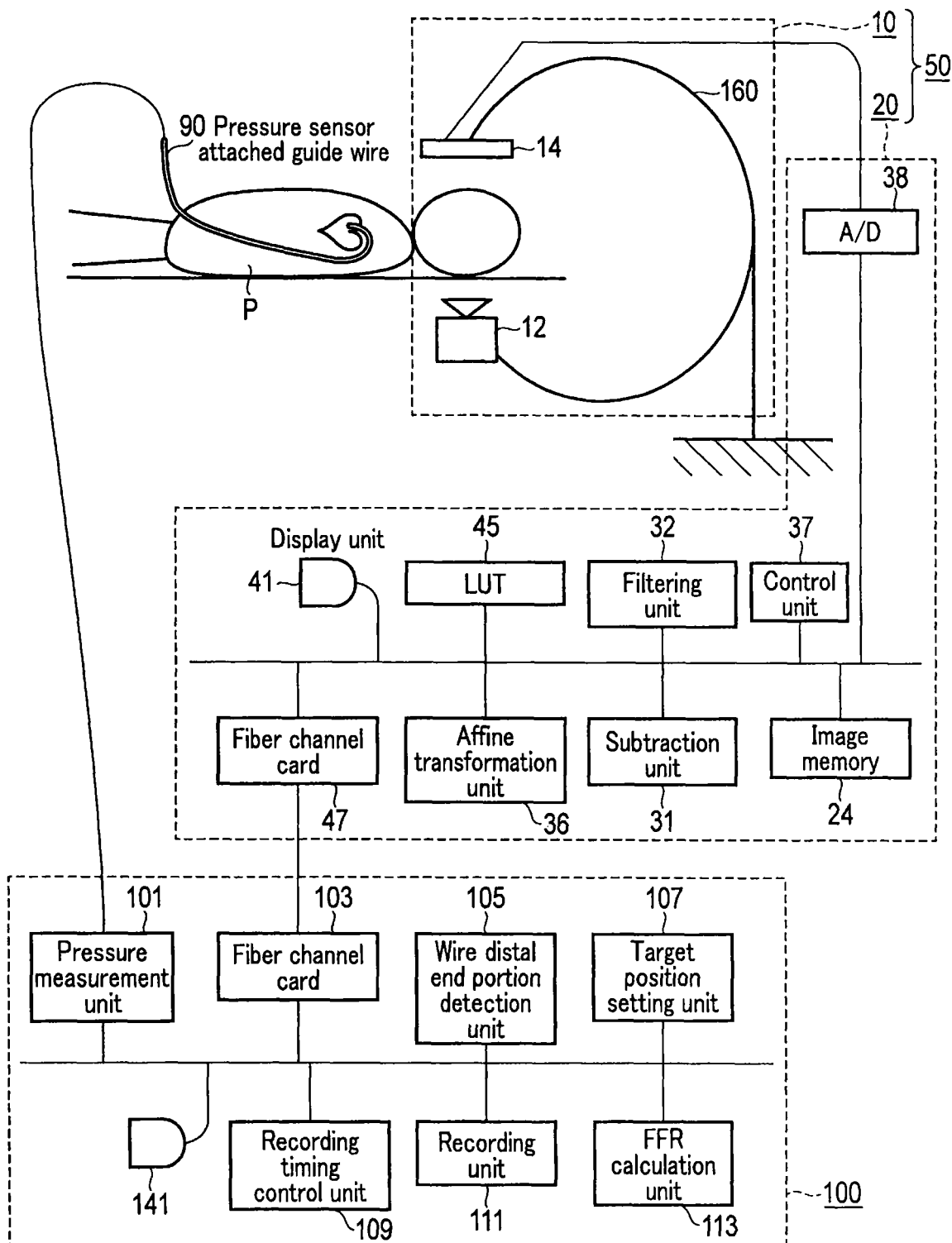
F I G. 1

BLOOD FLOW FUNCTION EXAMINATION APPARATUS AND X-RAY DIAGNOSTIC APPARATUS

CROSS-REFERENCE TO RELATED APPLICATIONS

This application is a Continuation Application of PCT Application No. PCT/JP2013/082271, filed Nov. 29, 2013 and based upon and claiming the benefits of priority from Japanese Patent Applications No. 2012-261261, filed Nov. 29, 2012, and No. 2013-248264, filed Nov. 29, 2013, the entire contents of all of which are incorporated herein by reference.

FIELD

Embodiments described herein relate generally to a blood flow function examination apparatus for examining a blood flow function and the like and an X-ray diagnostic apparatus including the blood flow function examination apparatus.

BACKGROUND

Recently, for example, in cases of vascular constriction, the increasing tendency is to perform medical treatment using a tubular member called a catheter instead of surgical treatment. In treatment using a catheter, the catheter is inserted into an object through, for example, the inguinal region, and is advanced to a constricted region along a blood vessel. A balloon is then inflated at the constricted region, thereby treating the region.

In addition, in order to prevent the occurrence of re-constriction, a mesh tube made of a metal, which is called a stent, is sometimes inserted into the constricted region to prevent re-constriction by internally supporting the wall of a blood vessel.

Obviously, medical treatment using the catheter described above, however, cannot 100% guarantee an improvement in symptom.

If, for example, a plurality of constricted regions exist in one blood vessel, it is very conceivable that a constricted region other than a constricted region having undergone treatment may actually greatly contribute to a reduction in blood flow. In such a case, the symptom does not improve unless this different constricted region contributing to the reduction in blood flow is treated.

In addition, in a worse case, the tissue of the distal end of the blood vessel may have undergone necrosis. In such a case, the symptom does not improve regardless of treatment on the constricted region because the tissue itself has already undergone necrosis.

In practice, there are an economic burden associated with treatment on a constricted region and a risk accompanying the treatment. For this reason, it can be said that any treatment on a constricted region, which does not contribute to an improvement in symptom as in the above case, should be avoided.

Under the above circumstances, an index called an FFR (Fractional Flow Reserve) is used to predict a treatment effect on a constricted region. An FFR is calculated by the following equation (1).

$$FFR=(Pd/Pp) \quad (1)$$

where Pd and Pp are the pressure values obtained by measurement upon insertion of a pressure sensor attached guide wire into a constricted region. Pp represents a pressure at a region nearer to the heart than the constricted region, and Pd represents a pressure at a region nearer to the peripheral side than the constricted region. That is, an FFR value can be obtained by calculating the ratio between pressures (blood pressures) before and after a constricted region. The necessities and the like of various types of treatments are determined based on such FFR values. In other words, an FFR is used, as an index for the functional evaluation of a coronary lesion, for coronary lesion evaluation. Note that various types of pressure sensor attached guide wires like that described above have been proposed.

In order to calculate an FFR, a cumbersome procedure is required, including an operation (pressing a recording button) for recording the measurement results (pressure data) obtained by the pressure sensor and a correcting operation, which are all manually performed while the pressure sensor attached guide wire is arranged before and after a constricted region, and an operation for stabilizing the guide wire is performed. In addition, if there are a plurality of lesions, the above procedure needs to be repeatedly executed for each lesion. Furthermore, the operator must always control the guide wire so as to prevent damage to the inner wall of a blood vessel and the like. For this reason, another person operates an apparatus for measuring an FFR.

It is therefore very conceivable that the operator may, for example, perform measurement at an improper position or forget to record measurement results. Even if the operator properly complete all the operations, it takes a considerable operation time.

In consideration of the above situation, it is an object to provide a blood flow function examination apparatus and an X-ray diagnostic apparatus which simplify a measurement procedure and shorten the operation time in blood flow function examination such as FFR measurement.

BRIEF DESCRIPTION OF THE DRAWINGS

FIG. 1 is a block diagram showing an example of the arrangement of a blood flow function examination apparatus according to the first embodiment of the present invention.

DETAILED DESCRIPTION

Figure 2:
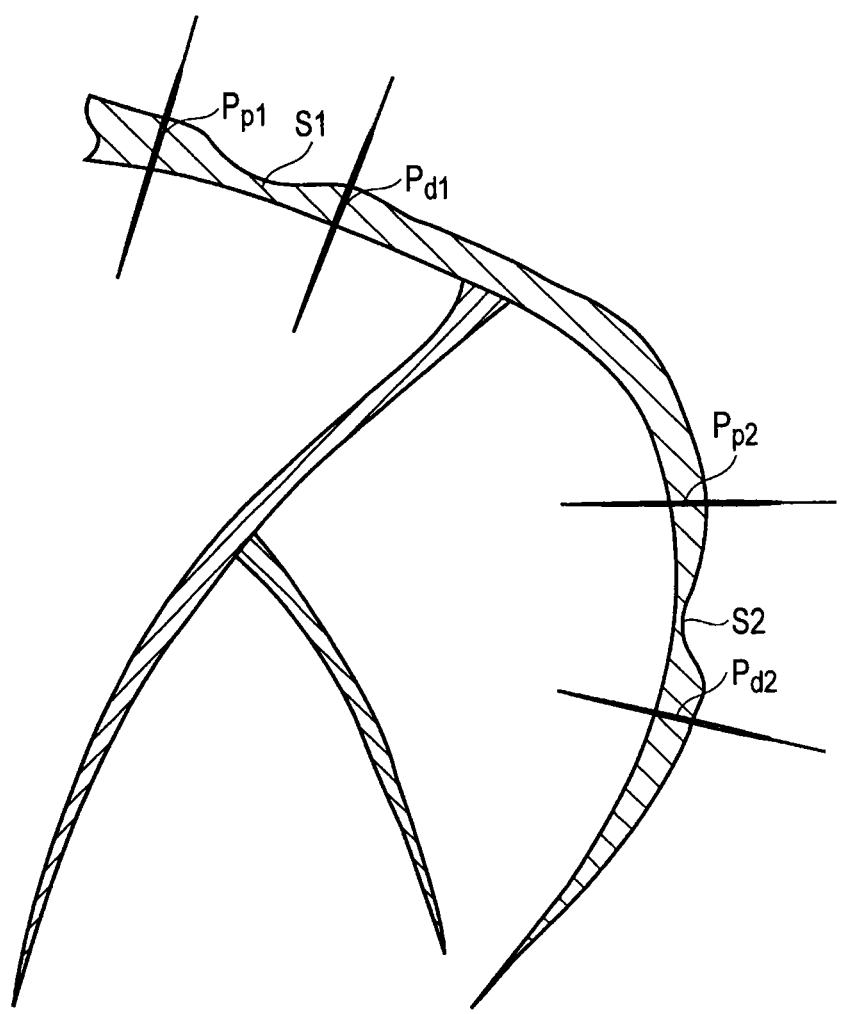
FIG. 2 is a view showing measurement positions on constricted regions in FFR calculation.

According to one embodiment, there is provided an X-ray diagnostic apparatus which comprises an X-ray generation unit configured to irradiate an object with X-rays; an X-ray detection unit configured to detect X-rays applied by the X-ray generation unit and transmitted through the object; an image generation unit configured to generate an X-ray image based on X-rays detected by the X-ray detection unit; a recording unit configured to record pressure data acquired by using a pressure sensor provided on a guide wire; a measurement position setting unit configured to set a measurement position for a pressure by the pressure sensor using the X-ray image; and a display unit configured to display the X-ray image almost in real time and superimpose and display the measurement position set by the measurement position setting unit.

FIG. 1 is a block diagram showing an example of the arrangement of a blood flow function examination apparatus according to the first embodiment of the present invention. As shown in FIG. 1, an X-ray diagnostic apparatus 50, a pressure sensor attached guide wire 90, and an electrocardiograph (not show) are communicably connected to a blood flow function examination apparatus 100 according to the first embodiment. Note that the following description will exemplify a case in which the blood flow function examination apparatus 100, which is formed separately from the X-ray diagnostic apparatus 50, implements processing associated with FFR calculation (to be described later). However, this example is not exhaustive, and the X-ray diagnostic apparatus 50 incorporating the function of the blood flow function examination apparatus 100 may implement the processing associated with FFR calculation.

The X-ray diagnostic apparatus 50 is an apparatus for providing an X-ray diagnostic image to the blood flow function examination apparatus 100, and includes an X-ray imaging mechanism 10 and an image processing apparatus 20.

The X-ray imaging mechanism 10 includes an X-ray tube 12, a detection system 14, a top 16 of a bed (not shown), and a C-arm 160.

The X-ray tube 12 is mounted on the C-arm 160 together with the detection system 14. In general, as the detection system 14, an FPD (Flat Panel Detector) is used. However, the detection system 14 may include an image intensifier and a TV camera. The C-arm 160 is suspended from the ceiling and supported on the column. The C-arm 160 is rotatable about three orthogonal axes. An object P placed on the top 16 of the bed (not shown) is arranged between the X-ray tube 12 and the detection system 14.

The image processing apparatus 20 includes a control unit 37, an A/D converter 38, an image memory 24, a subtraction unit 31, an affine transformation unit 36, a display unit 41, a lookup table (to be abbreviated as an LUT hereinafter) 45, a filtering unit 32, and a fiber channel card 47.

The control unit 37 comprehensively controls the respective units of the image processing apparatus 20. The A/D converter 38 is connected to the X ray imaging mechanism 10. The X ray imaging mechanism 10 digitizes projection data supplied as analog information. The image memory 24 stores the projection data supplied from the X ray imaging mechanism 10 and digitized by the A/D converter 38. The subtraction unit 31 executes image data subtraction (DSA: Digital Subtraction Angiography). The filtering unit 32 performs filtering processing such as harmonic enhancement processing. The affine transformation unit 36 performs enlargement processing and moving processing. The LUT 45 performs tone conversion for image data. The fiber channel card 47 is an I/F (interface) for fiber channel transfer.

The blood flow function examination apparatus 100 includes a pressure measurement unit 101, a fiber channel card 103, a wire distal end portion detection unit 105, a target position setting unit 107, a recording timing control unit 109, a recording unit 111, an FFR calculation unit 113, and a display unit 141.

The pressure measurement unit 101 receives an output signal (pressure data) from the pressure sensor of the pressure sensor attached guide wire 90, and calculates (measures) a pressure from the signal.

The fiber channel card 103 is an I/F (interface) for fiber channel transfer. In this case, the image processing apparatus 20 is connected to the blood flow function examination apparatus 100 via the fiber channel cards 47 and 103 and a fiber channel cable. The data acquired by the X-ray imaging mechanism 10 is configured to be transferred to the blood flow function examination apparatus 100 almost in real time by high-speed data Communication using the fiber channel cable.

The wire distal end portion detection unit 105 detects the distal end portion of the pressure sensor attached guide wire 90 from the X-ray diagnostic image transferred from the image processing apparatus 20. More specifically, the distal end portion of the pressure sensor attached guide wire 90 is provided with, for example, a radio-opaque marker (a marker formed from, for example, tungsten). In addition, the distal end portion of the pressure sensor attached guide wire 90 has a structure for improving visibility. The wire distal end portion detection unit 105 detects the distal end portion of the pressure sensor attached guide wire 90 by detecting this marker from an X-ray diagnostic image. In addition, the wire distal end portion detection unit 105 traces the distal end portion of the pressure sensor attached guide wire 90 by an image processing technique such as correlation computation.

As part of method 500 shown in FIG. 5, in step S510, the target position setting unit 107 sets a target position (a measurement position to be described later) where a pressure is measured (recorded) in advance, based on the X-ray diagnostic image transferred from the image processing apparatus 20.

The recording timing control unit 109 records the above pressure data on the recording unit 111 at a predetermined timing based on the position of the distal end portion of the pressure sensor attached guide wire 90 detected (in step S520 in FIG. 5) by the wire distal end portion detection unit 105 and the measurement position set by the target position setting unit 107. In other words, the recording timing control unit 109 controls the timing of recording pressure data on the recording unit 111 (generates a recording timing signal) based on the position of the distal end portion of the pressure sensor attached guide wire 90 and a measurement position.

Figure 5:
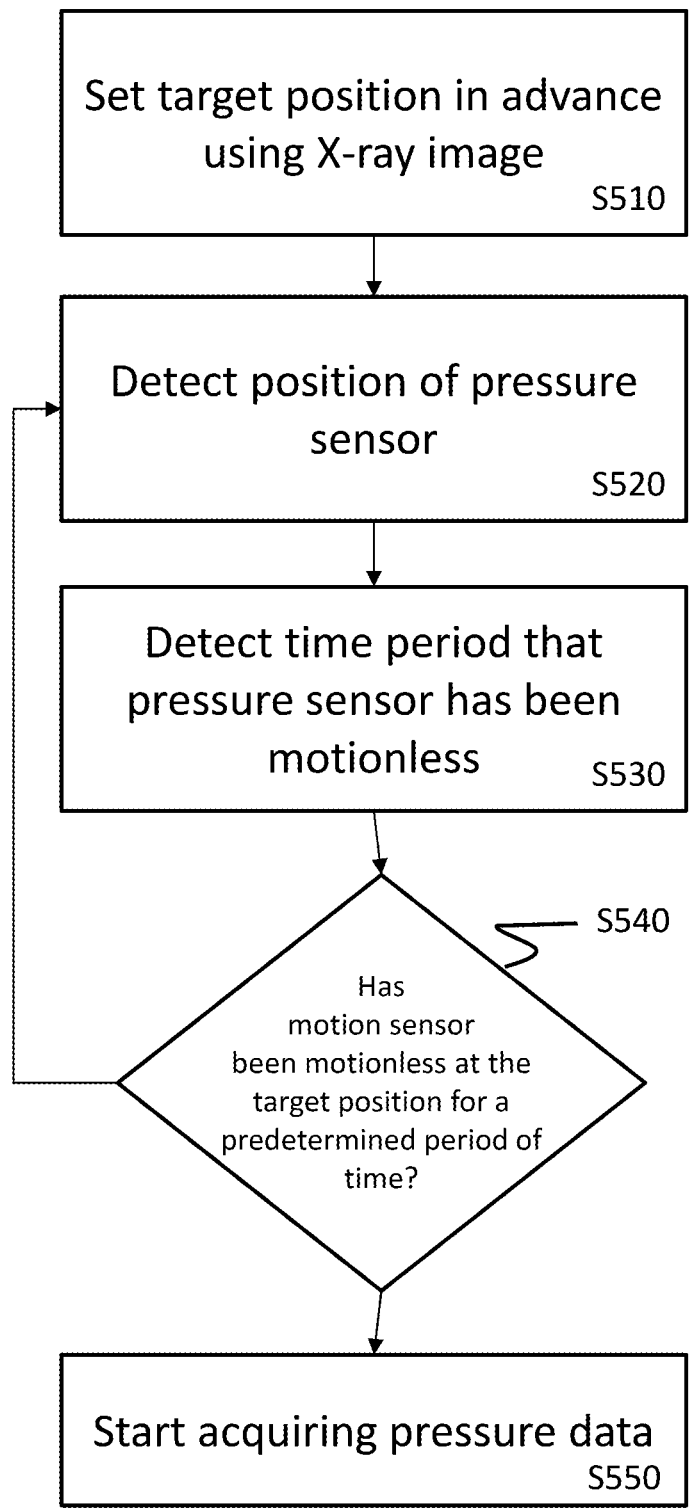
FIG. 5 shows the process performed by the processing circuitry.

More specifically, when the distal end portion of the pressure sensor attached guide wire 90 reaches the measurement position set in advance and it is detected (in step S530 in FIG. that the distal end portion is kept motionless for a predetermined time (as shown in step S540 of FIG. 5), the recording timing control unit 109 records the pressure data acquired by the pressure sensor at the measurement position on the recording unit 111 (as shown in step S550 in FIG. 5). Assume that the measurement position set in advance has a predetermined range.

The recording unit 111 records the pressure data acquired at each measurement position under the control of the recording timing control unit 109.

The FFR calculation unit 113 calculates a fractional flow reserve (to be abbreviated as an FFR hereinafter) based on the pressure data recorded on the recording unit 111. The FFR is an index for predicting a treatment effect on a constricted region. In this case, Pd and Pp are the pressure values obtained by measurement upon insertion of the pressure sensor attached guide wire into the constricted region. Letting Pp be a pressure at a region nearer to the heart than the constricted region, and Pd be a pressure at a region nearer to the peripheral side than the constricted region, the FFR is calculated by the following equation (2).

$$FFR = (Pd/Pp) \quad (2)$$

That is, an FFR value can be obtained by calculating the ratio of pressures at regions before and after a constricted region.

An example of a series of processing associated with FFR calculation by the blood flow function examination apparatus 100 according to the first embodiment of the present invention will be described below.

Note that when actually calculating an FFR by using the pressure sensor attached guide wire 90, it is necessary to perform various types of calibrations such as a calibration with an air pressure. However, these calibrations are not processing unique to the blood flow function examination apparatus according to the first embodiment, and hence a description of them will be omitted.

First of all, the user guides a catheter to the heart side of a blood vessel in which a constricted region is generated, and acquires X-ray diagnostic moving images (to be abbreviated as X-ray moving images hereinafter) by using the X-ray imaging mechanism 10 and the image processing apparatus 20 upon injecting a contrast medium through the catheter. At this time, if the blood vessel as an examination target is a cardiac blood vessel, the user simultaneously acquires an electrocardiogram by using an electrocardiograph (not shown) as well as the X-ray moving images. The images acquired by the X-ray imaging mechanism 10 and the image processing apparatus 20 are transmitted to the blood flow function examination apparatus 100 almost in real time.

The user refers to the X-ray moving images displayed on the display unit 141 of the blood flow function examination apparatus 100 to select an image which allows clear visual recognition of the constricted region and has a small amount of motion (e.g., the motion of the heart), and presses a "target position setting button".

FIG. 2 is a view showing measurement positions at a constricted region in FFR calculation. As shown in FIG. 2, the target position setting unit 107 sets measurement positions by drawing lines almost perpendicular to the blood vessel as a measurement target in the order from the heart side immediately near the constricted region to the peripheral side. In this case, if the blood vessel as an examination target is a cardiac blood vessel, an electrocardiographic phase when the heart is almost motionless is designated, and a measurement position on an X-ray image corresponding to the electrocardiographic phase is set. Each set measurement position is explicitly displayed on the X-ray image, as exemplarily shown in, for example, FIG. 2.

In this case, for a lesion including a plurality of constricted regions, this operation is repeated by the number of times corresponding to the number of constricted regions. In the case shown in FIG. 2, since there are a constricted region (1) S1 and a constricted region (2) S2, one straight line is drawn on each of the heart and peripheral sides of each of the two constricted regions. In this case, numbers ((1) and (2) in this case) are assigned to the constricted regions in the order in which the measurement positions were set.

Referring to FIG. 2, the line on the heart side of the constricted region (1) S1 indicates a measurement position for Pp1 (a blood pressure on the heart side of the constricted region (1) S1), and the line on the peripheral side indicates a measurement position for Pd1 (a blood pressure on the peripheral side of the constricted region (1) S1). Likewise, referring to FIG. 2, the line on the heart side of the constricted region (2) S2 indicates a measurement position for Pp2 (a blood pressure on the heart side of the constricted region (2) S2), and the line on the peripheral side indicates a measurement position for Pd2 (a blood pressure on the peripheral side of the constricted region (2) S2).

Upon determining that the target position setting unit 107 has properly set a measurement position, the user presses a "setting completion button". With this operation, measurement position information and electrocardiographic phase information (a position corresponding to a specific percent of an R-R signal) are transmitted to the recording timing control unit 109. Note that with regard to set measurement positions, it is possible to discriminate, based on electrocardiographic phase information, a state in which the measurement positions are displayed while being superimposed on a real-time image and a state in which the measurement positions are not displayed. It is also possible to sequentially update a real-time image on which measurement positions are superimposed and displayed, based on the electrocardiographic phase information. Subsequently, the user inserts the pressure sensor attached guide wire 90 into the catheter and exposes the pressure sensor attached guide wire 90 from the distal end portion of the catheter at a predetermined position nearer to the peripheral side than the constricted region (2) S2 while referring to the X-ray moving image displayed on the display unit 141. Note that the wire distal end portion detection unit 105 generates a subtraction image, with the movement of the pressure sensor attached guide wire 90 being extracted, by sequentially acquiring X-ray moving images from the X-ray diagnostic apparatus 50 in real time via the fiber channel cable and performing subtraction with respect to the image acquired at a given time point and the image acquired immediately before the given time point at least during the operation of the catheter or pressure sensor attached guide wire 90. At this time, if a blood vessel as an examination target is a cardiac blood vessel, a subtraction image, with the movement of the pressure sensor attached guide wire 90 being extracted, is generated by performing subtraction with respect to an image acquired in an electrocardiographic phase used to set a measurement position and an image acquired one cycle before the acquired image.

In addition, the wire distal end portion detection unit 105 extracts the both edges of the pressure sensor attached guide wire 90 from the subtraction image, and detects the distal end portion from the two extracted edges by using the feature amount of the distal end portion of the pressure sensor attached guide wire 90.

The user slowly moves the pressure sensor attached guide wire 90 into a blood vessel while pulling the catheter. The recording timing control unit 109 compares the detected distal end portion of the pressure sensor attached guide wire 90 with the measurement position information to determine whether the distal end portion of the pressure sensor attached guide wire 90 has entered a predetermined distance range from the measurement position and has been motionless for a predetermined time. In this case, if the blood vessel as an examination target is a cardiac blood vessel, the recording timing control unit 109 compares the distal end portion of the pressure sensor attached guide wire 90, detected from the image acquired at the electrocardiographic phase used for the setting of a measurement position, with the measurement position information to determine whether the distal end portion of the pressure sensor attached guide wire 90 has entered a predetermined distance range from the measurement position and has been motionless for a predetermined time. In this case, upon determining that the distal end portion of the pressure sensor attached guide wire 90 has entered the predetermined distance range from the measurement position and has been motionless for the predetermined time, the recording timing control unit 109 causes the display unit 141 of the blood flow function examination apparatus 100 to display, for example, the message "Blood pressure recording is started at the position on the heart side of the constricted region (2). Please fix the guide wire so as not to move it."

In addition, upon checking that the distance between the distal end portion of the pressure sensor attached guide wire 90 and the measurement position has not changed, the recording timing control unit 109 causes the display unit 141 to display, for example, the message "Blood pressure recording is being performed at the position on the heart side of the constricted region (2). Please fix the guide wire so as not to move it.", and records the pressure data at the measurement position on the recording unit 111 (generates a recording timing signal). That is, the recording unit 111 records the pressure data acquired by the pressure sensor at the measurement position under the control of the recording timing control unit 109 (in accordance with a recording timing signal).

When recording for a predetermined time is complete, the recording timing control unit 109 causes the display unit 141 to display the message "Blood pressure recording at the position on the heart side of the constricted region (2) is complete. Please move the guide wire to the next measurement position." When the recording operation is complete, the recording timing control unit 109 causes the display unit 141 to display a graph indicating the recorded pressure data (graph indicating a blood pressure variation at the measurement position).

The user then visually recognizes the graph displayed on the display unit 141 to determine whether a blood pressure has been properly measured. In this case, if, for example, the blood pressure variation has greatly changed in each cycle, since there is a possibility that the measurement has not been properly performed, the user presses a "re-measurement button" to execute re-measurement.

The above series of operations/processing for measurement is executed at each of the remaining measurement positions (i.e., the position on the peripheral side of the constricted region (1) S1, the position on the heart side of the constricted region (2) S2, and the position on the peripheral side in this case).

Upon completing calculation/recording of all the pressure data Pp1, Pd1, Pp2, and Pd2, the recording timing control unit 109 reads out the pressure data from the recording unit 111 and outputs them to the FFR calculation unit 113. The FFR calculation unit 113 then calculates the FFR values associated with all the constricted regions (the constricted region (1) S1 and the constricted region (2) S2 in this case) by substituting the pressure data (Pp1, Pd1, Pp2, and Pd2 in this case) recorded on the recording unit 111 into equation (2).

In addition, this embodiment includes the X-ray diagnostic apparatus 50 and the blood flow function examination apparatus 100 as separate apparatuses. Obviously, however, the blood flow function examination apparatus 100 may be built into the X-ray diagnostic apparatus 50. Alternatively, only the functions of some components of the blood flow function examination apparatus 100 may be built into the X-ray diagnostic apparatus 50. More specifically, the wire distal end portion detection unit 105, the target position setting unit 107, and the recording timing control unit 109 may be built into the X-ray diagnostic apparatus 50, and the X-ray diagnostic apparatus 50 may be configured to instruct a recording timing with respect to the blood flow function examination apparatus 100.

In addition, obviously, the first embodiment can be applied to not only FFR calculation but also CFR (Coronary Flow Reserve) calculation following a procedure similar to that for FFR.

As described above, the first embodiment can provide a blood flow function examination apparatus and an X-ray diagnostic apparatus which simplify a measurement procedure and shorten the operation time in blood flow function examination such as FFR measurement.

The blood flow function examination apparatus and the X-ray diagnostic apparatus according to the first embodiment described can be implemented upon being modified, for example, in the following manner.

First Modification

For example, in the above case, the FFR calculation unit 113 calculates FFRs at the time point when pressure data concerning all constricted regions (a constricted region (1) and a constricted region (2)) are calculated and recorded. However, FFRs may be sequentially calculated at the time point when Pp and Pd concerning one constricted region are calculated and recorded.

In addition, when an FFR value concerning a given constricted region becomes smaller than an "ischemic threshold" (for example, the "ischemic threshold" is 0.75, and the FFR value is calculated/recorded as 0.63), a graph of pressure data concerning the constricted region may be displayed on the display unit 141 to allow the user to check.

In addition, if an FFR value concerning a given constricted region becomes smaller than an "ischemic threshold" (for example, the "ischemic threshold" is 0.75, and the FFR value is calculated/recorded as 0.63), pressure data at the measurement positions concerning the constricted region may be acquired again to calculate an FFR again.

Second Modification

According to the above description, if it is determined that the distal end portion of the pressure sensor attached guide wire 90 has entered a predetermined distance range from a measurement position and has been motionless for a predetermined time, pressure data at the measurement position is automatically recorded on the recording unit 111. However, this example is not exhaustive. For example, the user may issue an instruction to start recording pressure data at a measurement position by performing a manual operation by himself/herself. In this case, it is preferable to cause the display unit 141 of the blood flow function examination apparatus 100 to display a message (or output a voice or the like) prompting to issue an instruction to start recording, for example, "Please press the blood pressure recording start button at a position on the heart side of the constricted region (2). Please fix the guide wire so as not to move it." in response to the arrival of the distal end portion of the pressure sensor attached guide wire 90 at the measurement position (or entrance into a predetermined distance range) as a trigger. In addition, it is possible to display a message informing that the above measurement is being executed and a message informing that the measurement is complete. In addition, assume that the distal end portion of the pressure sensor attached guide wire 90 has passed through the measurement position without the input of an instruction to start recording. In this case, it is preferable to cause the display unit 141 to display, for example, a warning message (or output a voice or the like) like "No blood pressure at the position on the heart side of the constricted region (2) has been recorded."

Third Modification

The position of the distal end portion of the pressure sensor attached guide wire 90 (i.e., the position of the pressure sensor) may be superimposed and displayed on an X-ray image in a form different from that of the surroundings (e.g., a different color, a different density, luminance inversion, blinking, or a combination of them).

Second Embodiment

A blood flow function examination apparatus and an X-ray diagnostic apparatus according to the second embodiment of the present invention will be described below. In order to avoid a redundant description, a difference from the first embodiment described above will be described. Note that like the first embodiment, the second embodiment will exemplify a case in which a blood flow function examination apparatus 100 formed separately from an X-ray diagnostic apparatus 50 implements the processing associated with FFR calculation to be described later. However, this case is not exhaustive, and the X-ray diagnostic apparatus 50 incorporating the function of the blood flow function examination apparatus 100 may implement the processing associated with FFR calculation.

According to the second embodiment, a position sensor (e.g., a GPS sensor) is provided on the distal end portion of a pressure sensor attached guide wire 90.

Figure 3:
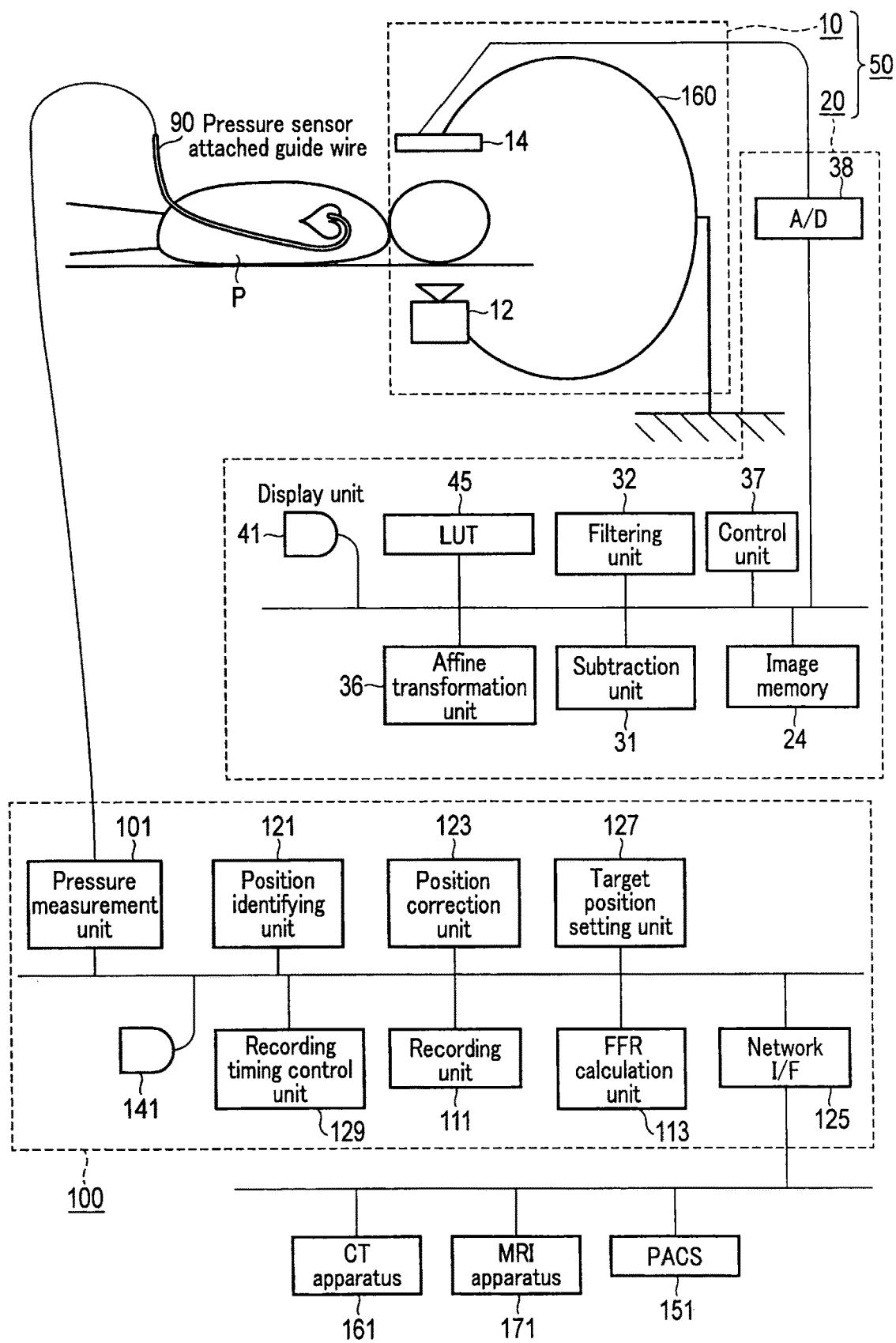
FIG. 3 is a block diagram showing an example of the arrangement of a blood flow function examination apparatus according to the second embodiment of the present invention.

FIG. 3 is a block diagram showing an example of the arrangement of a blood flow function examination apparatus according to the second embodiment of the present invention.

The main constituent elements different from those of the blood flow function examination apparatus 100 according to the first embodiment include a network I/F (InterFace) 125 for communicating with the outside using ETHERNET® or the like, a position identifying unit 121 for detecting the distal end portion of the pressure sensor attached guide wire 90 based on a signal (e.g., a GPS signal) from the position sensor, a target position setting unit 127 for setting the above measurement position in advanced based on a three-dimensional image such as a CT image or MRI image, a position correction unit 123 for calibration between a three-dimensional image such as a CT image or MRI image and the position sensor, and a recording timing control unit 129 for determining/controlling a recording timing based on output information from the position identifying unit 121 and output information from the target position setting unit 127.

A CT apparatus 161, an MRI apparatus 171, and a PACS 151 are communicably connected to the blood flow function examination apparatus 100 according to the second embodiment via the network interface 125.

An example of a series of processing associated with FFR calculation by the blood flow function examination apparatus according to the second embodiment of the present invention will be described below.

Note that when actually calculating an FFR by using the pressure sensor attached guide wire 90, it is necessary to perform various types of calibrations such as a calibration with an air pressure. However, these calibrations are not processing unique to the blood flow function examination apparatus according to the second embodiment, and hence a description of them will be omitted.

First of all, the user acquires three-dimensional images of a blood vessel as an examination target from the CT apparatus 161, the MRI apparatus 171, the PACS 151, and the like via the network interface 125. Such a three-dimensional image is a medical image depicting an area including a constricted region of a blood vessel as an examination target.

Figure 4:
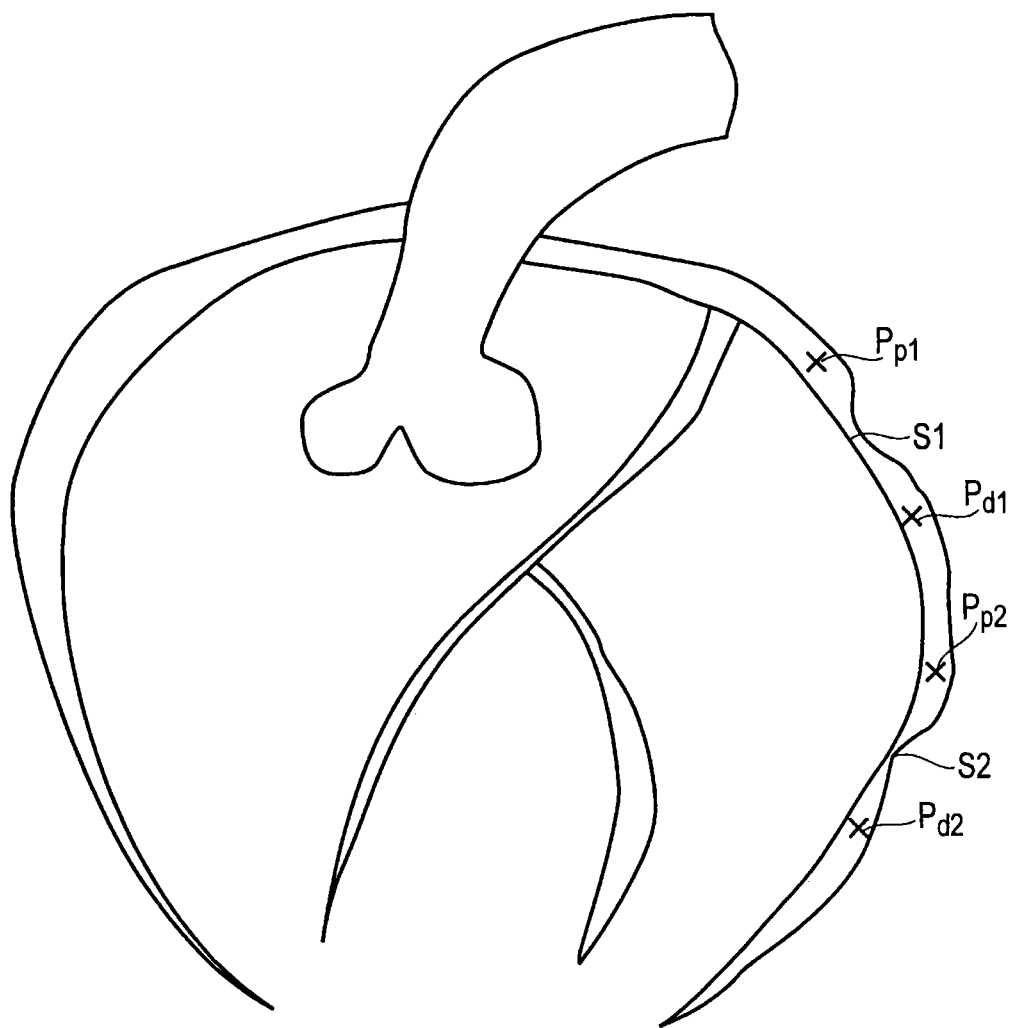
FIG. 4 is a view showing measurement positions on constricted regions in FFR calculation.

When the user presses a "target position setting button", the target position setting unit 127 identifies (detects) measurement positions, as shown in FIG. 4, in the order from the heart side immediately near the constricted region to the peripheral side on the three-dimensional image. FIG. 4 is a view showing measurement positions at constricted regions at the time of FFR calculation.

In this case, for a lesion including a plurality of constricted regions, this operation is repeated by the number of times corresponding to the number of constricted regions. In the case shown in FIG. 4, since there are a constricted region (1) S1 and a constricted region (2) S2, one mark is drawn on each of the heart and peripheral sides of each of the two constricted regions. In this case, numbers are assigned to the constricted regions in the order in which the measurement positions were set.

Referring to FIG. 4, the mark on the heart side of the constricted region (1) S1 indicates a measurement position for Pp1 (a blood pressure on the heart side of the constricted region (1) S1), and the mark on the peripheral side indicates a measurement position for Pd1 (a blood pressure on the peripheral side of the constricted region (1) S1). Likewise, the mark on the heart side of the constricted region (2) S2 indicates a measurement position for Pp2 (a blood pressure on the heart side of the constricted region (2) S2), and the mark on the peripheral side indicates a measurement position for Pd2 (a blood pressure on the peripheral side of the constricted region (2) S2).

Upon determining that a target position setting unit 107 has properly set a measurement position, the user presses a "setting completion button". With this operation, measurement position information and electrocardiographic phase information (a position corresponding to a specific percent of an R-R signal) from which a three-dimensional image is acquired are transmitted to a recording timing control unit 129.

Subsequently, the user advances the pressure sensor attached guide wire 90 through the catheter, and presses a "Calibration button". The position identifying unit 121 detects the distal end portion of the pressure sensor attached guide wire 90 based on a signal (e.g., a GPS signal) from the position sensor. When the distal end portion of the pressure sensor attached guide wire 90 reaches a characteristic structure of the blood vessel, the position identifying unit 121 specifies a position on the three-dimensional image which corresponds to the position of the distal end portion of the pressure sensor attached guide wire 90. This series of operations/processing is executed three times.

Subsequently, the coordinates on the three-dimensional image of the blood vessel as an examination target, which are specified by the above processing, and the three-dimensional coordinates detected by a signal (e.g., a GPS signal) from the position sensor are transmitted to the position correction unit 123. The position correction unit 123 performs calibration between the three-dimensional image and the position sensor based on these pieces of transmitted information. This completes the association (position correction processing) between the three-dimensional coordinates detected by the position sensor provided on the distal end portion of the pressure sensor attached guide wire 90 and the three-dimensional coordinates on the three-dimensional image of the blood vessel as an examination target.

After the completion of the position correction processing by the above processing, the user inserts the pressure sensor attached guide wire 90 into the catheter and exposes the pressure sensor attached guide wire 90 from the distal end portion of the catheter at a predetermined position nearer to the peripheral side than the constricted region (2) S2 while referring to the X-ray moving image displayed on a display unit 141.

The position identifying unit 121 converts a signal (e.g., a GPS signal) from the position sensor provided on distal end portion of the pressure sensor attached guide wire 90 into three-dimensional coordinates. In addition, the position correction unit 123 converts (corrects) the three-dimensional coordinates into three-dimensional coordinates on a three-dimensional image the blood vessel. The three-dimensional coordinates after this conversion are displayed as the position of the pressure sensor attached guide wire 90 on the three-dimensional image of the blood vessel displayed on the display unit 141, and are transmitted to the recording timing control unit 129 almost in real time.

The recording timing control unit 129 then compares the detected distal end portion of the pressure sensor attached guide wire 90 with the measurement position information to determine whether the distal end portion of the pressure sensor attached guide wire 90 has entered a predetermined distance range from the measurement position and have been motionless for a predetermined time.

In this case, upon determining that the distal end portion of the pressure sensor attached guide wire 90 has entered the predetermined distance range from the measurement position and has been motionless for the predetermined time, the recording timing control unit 129 causes the display unit 141 of the blood flow function examination apparatus 100 to display, for example, the message "Blood pressure recording is started at the position on the heart side of the constricted region (1). Please fix the guide wire so as not to move it."

In addition, upon checking that the distance between the distal end portion of the pressure sensor attached guide wire 90 and the measurement position has not changed, the recording timing control unit 129 causes the display unit 141 to display, for example, the message "Blood pressure recording is being performed at the position on the heart side of the constricted region (1). Please fix the guide wire so as not to move it.", and records the pressure data at the measurement position on a recording unit 111 (generates a recording timing signal). That is, the recording unit 111 records the pressure data acquired by the pressure sensor at the measurement position under the control of the recording timing control unit 129 (in accordance with a recording timing, signal).

When recording for a predetermined time is complete, the recording timing control unit 129 causes the display unit 141 to display the message "Blood pressure recording at the positions on the heart side of the constricted region (1) is complete. Please move the guide wire to the next measurement position." When the recording operation is complete, the recording timing control unit 129 causes the display unit 141 to display a graph indicating the recorded pressure data (graph indicating a blood pressure variation at the measurement position).

The user then visually recognizes the graph displayed on the display unit 141 to determine whether a blood pressure has been properly measured. In this case, if, for example, the blood pressure variation has greatly changed in each cycle, since there is a possibility that the measurement has not been properly performed, the user presses a "re-measurement button" to execute re-measurement.

The above series of operations/processing is executed at each of the remaining measurement positions (i.e., the position on the peripheral side of the constricted region (1) S1, the position on the heart side of the constricted region (2) S2, and the position on the peripheral side in this case). Upon completing calculation/recording of all the pressure data Pp1, Pd1, Pp2, and Pd2, the recording timing control unit 129 reads out the pressure data from the recording unit 111 and outputs them to an FFR calculation unit 113. The FFR calculation unit 113 then calculates the FFR values associated with all the constricted regions (the constricted region (1) S1 and the constricted region (2) S2 in this case) by substituting the pressure data (Pp1, Pd1, Pp2, and Pd2 in this case) recorded on the recording unit 111 into equation (2).

Modification

Obviously, the FFR calculation timing (first modification) described in the first embodiment, the control on the start of recording of pressure data by manual operation (second modification), and the display form of the position detected by the pressure sensor (third modification) can also be applied the second embodiment.

As described above, the second embodiment can provide a blood flow function examination apparatus and an X-ray diagnostic apparatus which have the same effects as those of the blood flow function examination apparatus and the X-ray diagnostic apparatus according to the first embodiment. Note that if the blood vessel as an examination target is a cardiac blood vessel, the distal end portion of the pressure sensor attached guide wire 90, detected from the image acquired in the electrocardiographic phase used for the setting of a measurement position, may be compared with the measurement position information to determine whether the distal end portion of the pressure sensor attached guide wire 90 has entered a predetermined distance range from the measurement position and has been motionless for a predetermined time.

Although several embodiments of the present invention have been described above, they are presented as examples and not intended to limit the scope of the present invention.

For example, each embodiment described above has exemplified the case in which the X-ray diagnostic apparatus is used as a medical image diagnostic apparatus. However, this example is not exhaustive, and the above blood flow function examination may be implemented by using other medical diagnostic apparatuses such as an X-ray computed tomography apparatus, a magnetic resonance imaging apparatus, and an ultrasonic diagnostic apparatus.

In addition, these novel embodiments can be implemented in other various forms, and various omissions, replacements, and changes can be made without departing from the spirit of the present invention. These embodiments and their modifications are incorporated in the scope and sprit of the present invention, and are also incorporated in the scope of the invention and its equivalents defined in the appended claims.

What is claimed is:
1. An X ray diagnostic apparatus, comprising:
an X-ray tube configured to irradiate an object with X-rays;
an X-ray detector configured to detect X-rays applied by the X-ray tube and transmitted through the object;

an image processing circuit configured to generate an X-ray image based on X-rays detected by the X-ray detector;

processing circuitry configured to
set a target position using the X-ray image, in advance, at which to measure pressure using a pressure sensor, the pressure sensor being provided on a guide wire;
detect a position of a distal end of the pressure sensor in the object;
determine, by using a comparison between the target position set in advance using the X-ray image and positions of the distal end of the pressure sensor on a plurality of X-ray images acquired in a same electrocardiographic phase, if the distal end of the pressure sensor reaches the target position and the distal end of the pressure sensor on the plurality of X-ray images stays motionless for a predetermined motionless-pressure-sensor period at the target position set in advance using the X-ray image, wherein the predetermined motionless-pressure-sensor period is an amount of time used to indicate, by the distal end of the pressure sensor remaining motionless at the target position for that amount of time, that pressure data should begin to be acquired; and
start to acquire pressure data by using the pressure sensor at the target position based on having determined that the distal end of the pressure sensor on the plurality of X-ray images reached the target position set in advance using the X-ray image and the distal end of the pressure sensor on the plurality of X-ray images stayed motionless for the predetermined motionless-pressure-sensor period at the target position set in advance using the X-ray image;
a memory to record pressure data acquired by using the pressure sensor; and
a display capable of displaying the X-ray image and a first drawing representing the target position.

2. The X ray diagnostic apparatus of claim 1, wherein the processing circuitry is further configured to cause the first drawing to be displayed or not displayed based on electrocardiographic phase information.

3. The X ray diagnostic apparatus of claim 1, wherein the processing circuitry is further configured to cause the display to update the X-ray image in real time, based on electrocardiographic phase information.

4. The X ray diagnostic apparatus of claim 1, wherein the processing circuitry is further configured to cause the display to display a second drawing representing the detected position of the pressure sensor in a form including at least one of a different color, density, luminance inversion, and blinking.

5. The X ray diagnostic apparatus of claim 1, wherein the processing circuitry is further configured to
correct the detected position of the pressure sensor based on a position information signal output from the position sensor provided on the guide wire and a coordinate system of the X ray image, and
determine, based on the corrected position of the pressure sensor, whether the pressure sensor stays motionless at the set target position for the predetermined motionless-pressure-sensor period.

6. The X ray diagnostic apparatus of claim 1, wherein the processing circuitry is further configured to present a user with a first message indicating a start time of recording of the pressure data in the memory when recording of the pressure data starts, and present the user with a second message indicating that recording processing is being performed when the recording processing is being performed.

7. The X ray diagnostic apparatus of claim 6, wherein the first message presented to the user by the processing circuitry includes at least one of a message informing a start of recording in a short time and a message prompting to fix a position of the guide wire.

8. The X ray diagnostic apparatus of claim 6, wherein the second message presented to the user by the processing circuitry includes at least one of a message indicating that recording is being performed and a message requesting to keep the guide wire motionless.

9. The X ray diagnostic apparatus of claim 1, wherein the processing circuitry is further configured to present a user with at least one of a message indicating completion of recording upon completion of recording of the pressure change on the memory and a message permitting the user to move the guide wire.

10. The X ray diagnostic apparatus of claim 1, wherein when recording of the pressure data on the memory is complete, the processing circuitry is further configured to cause the display to display a graph indicating the recorded pressure.

11. The X ray diagnostic apparatus of claim 1, wherein when recording of the pressure data on the memory is complete, the processing circuitry is further configured to calculate a fractional flow reserve value based on the recorded pressure data, and when the value is not more than a predetermined threshold, the processing circuitry is further configured to record again the pressure data at a same target position in the memory.

12. The X ray diagnostic apparatus of claim 1, wherein when recording of the pressure data associated with the target position is complete, the processing circuitry is further configured to change a display form of the first drawing on the X ray image displayed on the display.

13. The X ray diagnostic apparatus of claim 1, wherein when recording of the pressure data associated with the target position is incomplete, the processing circuitry is further configured to display a warning to prompt a user to record the pressure data at the target position.

14. The X ray diagnostic apparatus of claim 1, wherein the processing circuitry is further configured to set a target position based on a constricted region of a blood vessel expressed by the X-ray image.

15. The X ray diagnostic apparatus of claim 14, wherein the processing circuitry is further configured to set the target position before and after the constricted region.

16. The X ray diagnostic apparatus of claim 14, wherein the processing circuitry is further configured to set and display the target position on the display based on the constricted region expressed by the X-ray image and user input.

17. An X ray diagnostic apparatus, comprising:
an X-ray tube configured to irradiate an object with X-rays;
an X-ray detector configured to detect X-rays applied by the X-ray tube and transmitted through the object;
an image processing circuit configured to generate an X-ray image based on X-rays detected by the X-ray detector;
processing circuitry configured to
set a target position in advance at which to measure pressure using a pressure sensor, using the X-ray image, the pressure sensor being provided on a guide wire;

detect a position of a distal end of the pressure sensor in the object;

determine, by using a comparison between the target position set in advance using the X-ray image and the position of the distal end of the pressure sensor on a plurality of X-ray images acquired in a same electrocardiographic phase, if the distal end of the pressure sensor reaches the target position and the distal end of the pressure sensor on the plurality of X-ray images stays motionless for a predetermined motionless-pressure-sensor period at the target position set in advance using the X-ray image, wherein the predetermined motionless-pressure-sensor period is an amount of time used to indicate, by the distal end of the pressure sensor remaining motionless at the target position for that amount of time, that pressure data should begin to be acquired;

start to acquire pressure data by using the pressure sensor at the target position based on having determined that the distal end of the pressure sensor on the plurality of X-ray images reached the target position set in advance using the X-ray image and the distal end of the pressure sensor on the plurality of X-ray images stayed motionless for the predetermined motionless-pressure-sensor period at the target position set in advance using the X-ray image; and display the X-ray image and a first drawing representing the target position; and a memory to record pressure data acquired by using the pressure sensor.

\* \* \* \* \*